(12) United States Patent
Gearwar (10) Patent No.: US 11,259,826 B2
(45) Date of Patent: Mar. 1, 2022

(54) APPARATUS FOR REMOVING A HOOK WITH A BARB

(71) Applicant: Gearwar LLC, Castle Hayne, NC (US)

(72) Inventor: David Gearwar, Lake George, NY (US)

(73) Assignee: Gearwar LLC, Castle Hayne, NC (US)

( * ) Notice: Subject to any disclaimer, the term of this patent is extended or adjusted under 35 U.S.C. 154(b) by 251 days.

(21) Appl. No.: 15/983,360

(22) Filed: May 18, 2018

(65) Prior Publication Data
US 2019/0350606 A1 Nov. 21, 2019

(51) Int. Cl.
*A61B 17/28* (2006.01)
*A61B 17/00* (2006.01)

(52) U.S. Cl.
CPC ........ *A61B 17/282* (2013.01); *A61B 17/2841* (2013.01); *A61B 2017/0042* (2013.01); *A61B 2017/00747* (2013.01); *A61B 2017/2808* (2013.01)

(58) Field of Classification Search
CPC ... A61B 17/282; A61B 17/2841; A61B 17/50; A61B 17/285; A61B 2017/00747; A61B 2017/0042; A61B 2017/2808; A01K 97/18
See application file for complete search history.

(56) References Cited

U.S. PATENT DOCUMENTS

| | | | | |
|---|---|---|---|---|
| 505,835 A * | 10/1893 | Kulp et al. | ............... | A44C 5/02 7/101 |
| 979,609 A * | 12/1910 | Vaughn | ..................... | B21L 1/02 59/27 |
| 1,328,423 A * | 1/1920 | Davies | .................. | B65B 13/025 140/121 |
| 3,277,895 A * | 10/1966 | Johnson | ............. | A61B 17/2812 606/158 |
| 3,778,919 A | 12/1973 | Simon | | |
| 4,226,241 A | 10/1980 | Walker, Jr. | | |
| 5,397,326 A | 3/1995 | Mangum | | |
| 5,421,120 A * | 6/1995 | Brumfield | .............. | A01K 97/18 43/53.5 |
| 5,922,008 A | 7/1999 | Gimpelson | | |
| 6,146,392 A * | 11/2000 | Smith | .................. | A61B 17/062 606/145 |
| 6,205,699 B1 | 3/2001 | Bogni | | |

(Continued)

FOREIGN PATENT DOCUMENTS

CN 105534571 A 5/2016

OTHER PUBLICATIONS

International Search Report and Written Opinion of the International Searching Authority for International Application No. PCT/US2019/061910 dated Feb. 3, 2020.

(Continued)

*Primary Examiner* — Anh T Dang
(74) *Attorney, Agent, or Firm* — Dentons Cohen & Grigsby P.C.

(57) ABSTRACT

An apparatus for removing a hook embedded within a tissue is presented. The hook has a barb extending from a point section of the hook. The apparatus includes a clamping device configured to secure the hook. A probe is coupled to the clamping device. The probe has a tip portion configured to fit within a space between the barb and the point section of the hook to allow the hook to be removed from the tissue.

12 Claims, 10 Drawing Sheets

(56) References Cited

U.S. PATENT DOCUMENTS

| | | | |
|---|---|---|---|
| 6,293,954 B1 * | 9/2001 | Fogarty | A61B 17/282 |
| | | | 606/151 |
| 8,663,269 B2 | 3/2014 | Randall | |
| 9,216,029 B1 | 12/2015 | Hagn et al. | |
| 9,565,842 B1 | 2/2017 | Winter | |
| 2008/0154300 A1 | 6/2008 | Jabbour | |
| 2012/0037537 A1 * | 2/2012 | Schein | B65D 75/368 |
| | | | 206/703 |
| 2016/0235498 A1 | 8/2016 | Stanley et al. | |

OTHER PUBLICATIONS

Gammons, M., et al., "Fishhook Removal", American Family Physician, vol. 63, No. 11, pp. 2231-2236 (2001).

* cited by examiner

APPARATUS FOR REMOVING A HOOK WITH A BARB

TECHNICAL FIELD

The present disclosure relates to apparatus and methods for removing hooks from tissue. More specifically, the disclosure relates to examples of an apparatus for removing a hook embedded within a tissue, wherein the hook has a barb extending from a point section of the hook, and methods for performing the same.

BACKGROUND

Hooks with barbs are used to penetrate tissue with a point disposed on a point section of the hook. The bard, which is also disposed on the point section but which extends in an opposite direction to that of the point, is used to prevent the hook from being disgorged from the tissue.

One of the most common type of hooks with barbs are fish hooks. A fish hooks is a device for catching fish by impaling them in, for example, the mouth. There is an enormous variety of fish hooks in the world of fishing. Sizes, designs, shapes, and materials are all variable depending on the intended purpose of the fish hook. Fish hooks are manufactured for a range of purposes from general fishing to extremely limited and specialized applications.

The parts of a basic fish hook are as follows:

The point, which is the sharp end that penetrates the fish's mouth or flesh. The point is disposed on the point section of the hook.

The barb, which is the projection extending backwards from the point, that secures the fish from unhooking. The barb is also disposed on the point section of the hook.

The eye, which is the loop in the end of the hook that is connected to a fishing line or lure.

The shank, which is that portion of the hook that connects the eye to the point section.

Finally, the bend, or bend section, is the curved part of the shank that is connected to the point section.

Care needs to be taken when handling hooks as they can impale a user. If a hook goes in deep enough below the barb, pulling the hook out will tear the flesh. Accordingly, removing a fish hook impaled in a user can be a traumatic experience for the user.

Moreover, fish are often caught and released for a variety of reasons. For example, fish are often released due to the catch and release nature of sport fishing. Also, fish may be released because they are too small, too immature or the wrong sex.

However, the bard of a fish hook can cause severe injury to the fish that are intended to be released. Often the fish will be released only to die a short time later due to injuries inflicted by the barb when the hook was being removed.

Accordingly, there is a need for an apparatus for enabling the removal of a hook with a barb that is embedded within flesh or tissue. There is also a need for an apparatus that prevents the bard from tearing the tissue upon removal from the tissue. Further, there is a need for a method of removing a hook with a barb from tissue such that the damage to the tissue caused by the barb is reduced or eliminated.

BRIEF DESCRIPTION

The present disclosure offers advantages and alternatives over the prior art by providing an apparatus for removing a hook with a barb from tissue such as human flesh or the flesh of a fish. The apparatus prevents, or significantly reduces, damage to the tissue caused by the barb when the barb is being removed.

An apparatus for removing a hook having a barb extending from a point section of the hook, wherein the hook is embedded within a tissue, in accordance with one or more aspects of the present disclosure, includes a clamping device configured to secure the hook. A probe is coupled to the clamping device. The probe has a tip portion configured to fit within a space between the barb and the point section of the hook to allow the hook to be removed from the tissue.

An alternative apparatus for removing a hook having a barb extending from a point section of the hook, wherein the hook is embedded within a tissue, in accordance with one or more aspects of the present disclosure, includes a forceps configured to secure the hook. The forceps include a first arm pivotally connected to second arm. The first arm has a first jaw disposed on a first distal end portion and a first finger grip section disposed on a first proximal end portion. The second arm has a second jaw disposed on a second distal end portion and a second finger grip section disposed on a second proximal end portion. A probe handle is pivotally coupled to the forceps. The probe handle includes a distal end portion and a proximal end portion. The proximal end portion has a finger grip section sized to engage a finger. A probe is pivotally coupled to the distal end portion of the probe handle. The probe has a tip portion configured to fit within a space between the barb and the point section of the hook to allow the hook to be removed from the tissue.

A method of removing a hook embedded within tissue in accordance with one or more aspects of the present disclosure is also presented. The hook includes a point section. The point section has a barb and a point extending therefrom in opposing directions. The point of the hook has entered the tissue at an area of entry on the tissue to create a wound in the tissue. The method includes providing an apparatus for removing the hook embedded within the tissue. The apparatus includes a clamping device configured to secure the hook. A probe is pivotally coupled to the clamping device. The probe has a tip portion configured to fit within a space between the barb and the point section of the hook. The method further includes grasping the hook with the clamping device. The probe is then inserted into the area of entry of the wound. The tip portion of the probe is then fitted within a space between the barb and the point section of the hook to form a surface between the probe and the barb which allows the hook to be removed from the tissue without the barb digging into the tissue. The hook is then removed from the tissue, wherein, due to the surface formed between the probe and the barb, further damage to the tissue by the barb is significantly reduced compared to further damage to the tissue caused by the hook being removed without formation of the aforementioned surface.

DRAWINGS

The disclosure will be more fully understood from the following detailed description taken in conjunction with the accompanying drawings, in which.

DETAILED DESCRIPTION

Certain examples will now be described to provide an overall understanding of the principles of the structure, function, manufacture, and use of the methods, systems, and devices disclosed herein. One or more examples are illustrated in the accompanying drawings. Those skilled in the art will understand that the methods, systems, and devices specifically described herein and illustrated in the accompanying drawings are non-limiting examples and that the scope of the present disclosure is defined solely by the claims. The features illustrated or described in connection with one example may be combined with the features of other examples. Such modifications and variations are intended to be included within the scope of the present disclosure.

The terms "substantially", "approximately", "about", "relatively," or other such similar terms that may be used throughout this disclosure, including the claims, are used to describe and account for small fluctuations, such as due to variations in processing. For example, they can refer to less than or equal to ±10%, such as less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

FIGS. 1A-4 illustrate various examples of an apparatus for removing a hook with a barb from tissue according to aspects described herein. FIGS. 5-8 illustrate various examples of a method of utilizing the apparatus to remove a hook with a barb from tissue according to aspects described herein.

Figure 1A:
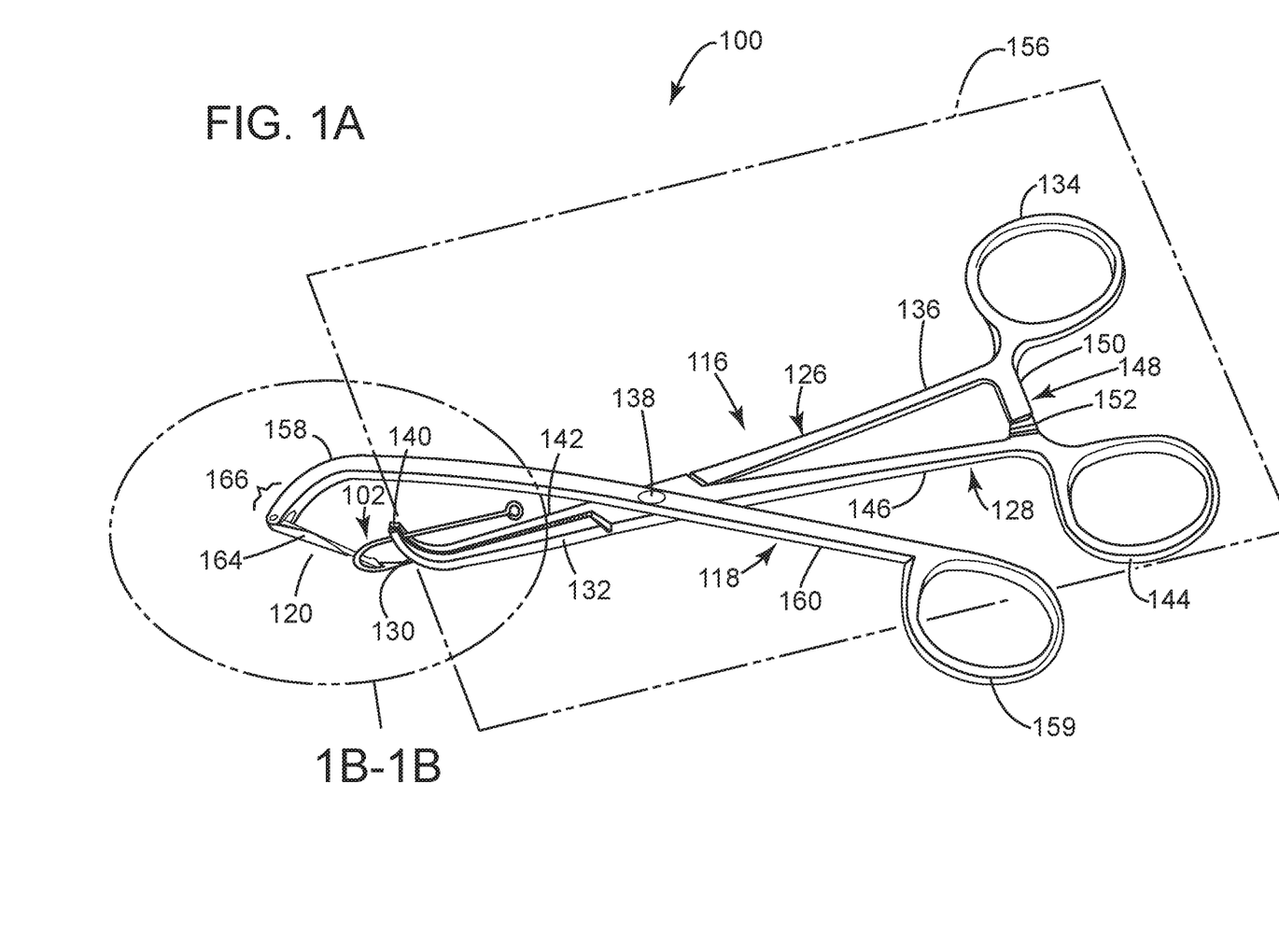
FIG. 1A depicts a perspective view of an example of an apparatus for removing a hook embedded within a tissue according to aspects described herein.
Figure 1B:
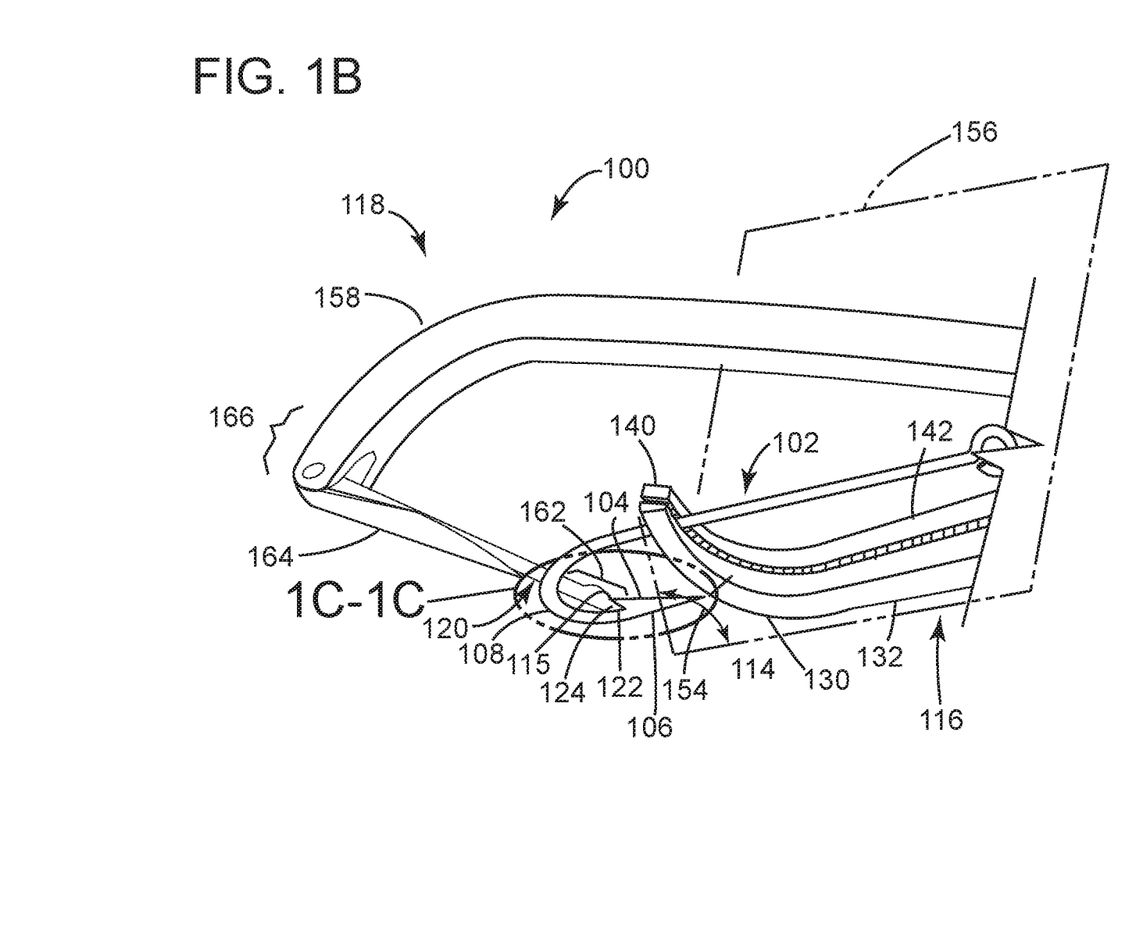
FIG. 1B depicts an expanded perspective view of the circled area 1B-1B of FIG. 1A, wherein the apparatus includes a probe, and wherein a tip portion of the probe includes a protrusion, according to aspects described herein.
Figure 1C:
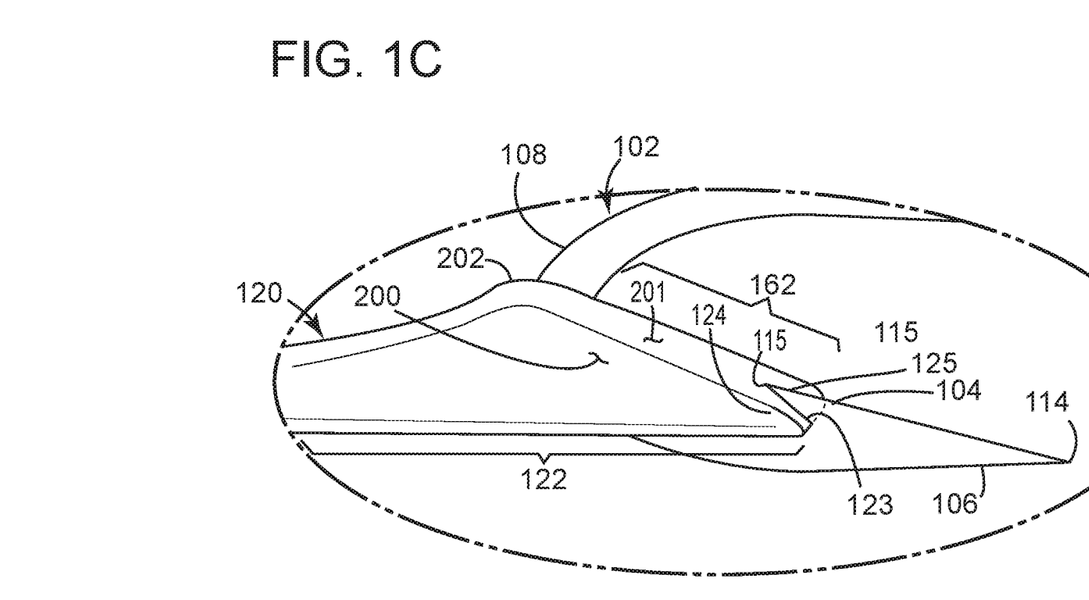
FIG. 1C depicts an expanded perspective view of the circled area of 1C-1C of FIG. 1B according to aspects described herein.

Referring to FIGS. 1A, 1B and 1C, an example of an apparatus 100 for removing a hook 102 is depicted. More specifically, FIG. 1A depicts an example of a perspective view of an apparatus 100 for removing a hook 102 with a barb 104 from tissue 184 (best seen in FIGS. 5-8). Additionally FIG. 1B depicts an expanded perspective view of the circled area 1B-1B of FIG. 1A. Additionally, FIG. 1C depicts an expanded perspective view of the circled area of 1C-1C of FIG. 1B.

The basic structure of hook 102 (best seen in FIG. 1B) includes a point section 106, a shank 110, a bend section 108 of the shank 110 and an eye 112. For purposes herein, the shank 110 includes the bend (or bend section) 108 plus the straight portion of the hook from the bend 108 to the eye 112. Disposed on the most distal end of the point section 106 is a point 114 of the hook 102, which is utilized to penetrate various tissues (such as the mouth of a fish or other parts of a fish's body). Also disposed on the point section 106 is the barb 104, which extends in an opposing direction relative to the point 114. Disposed on the most distal end of the barb 104 is the point 115 of the barb 104. The function of the barb 104 is to prevent the removal of the hook 102 once the point section 106 is embedded within tissue 184. The bend 108 is the curved part of the hook 102 that is connected to the point section 106. The eye 112 is the looped end of the hook 102 that is connected to a fishing lure (not shown). Finally, the shank 110 is that portion of the hook 102 that connects the eye 112 to the point section 106. The shank 110 includes the bend 108 plus the straight portion of the hook that connects the eye 112 to the bend 108.

The basic structure of apparatus 100 (best seen in FIG. 1A) includes a clamping device 116, a probe handle 118 and a probe 120. The clamping device 116 is configured to secure the hook 102. The probe 120 is coupled to the clamping device 116 through the probe handle 118. The probe 120 has a tip portion 122 that is configured to fit within a space 124 between the barb 104 and the point section 106 of the hook 102.

In the specific example illustrated in FIG. 1A, the clamping device 116 is a forceps 116. However other types of clamping devices 116 may also be used to secure the hook 102 and guide the probe 120. For example, the clamping device 116 may include various forms of gripping tools, such as a needle nose pliers, hemostats or the like. The clamping device 116 may be pivotally attached to a guide lever (similar to probe handle 118), wherein the guide lever can be used to guide the probe 120 into a wound.

The forceps 116 include a first arm 126 and a second arm 128. The first arm 126 has a first jaw 130 disposed on a first distal end portion 132 and a first finger grip section 134 disposed on a first proximal end portion 136. In this particular example, the finger grip section 134 is configured as a loop sized to receive a finger therein. However the finger grip section 134 may have other configurations as well, for example, the finger grip section may be configured as a straight member with a rough surface upon which a finger can be placed.

The second arm 128 is pivotally connected to the first arm 126 at a pivot joint 138. The pivot joint 138 can be any one of several well-known pivot joints, for example, the pivot joint 138 maybe a configured as a pivot bolt and nut assembly.

The second arm 128 has a second jaw 140 disposed on a second distal end portion 142. It is the combination of the first jaw 130 and second jaw 140 that are used to secure the hook 102 by clamping onto the shank 110 of the hook.

The second arm 128 also includes a second finger grip section 144 disposed on a second proximal end portion 146. In this particular example, the finger grip section 144 is configured as a loop sized to receive a finger therein. However the finger grip section 144 may have other configurations as well.

A ratcheting mechanism 148 is disposed on the first and second arms 126, 128 of the forceps 116. More specifically, the ratcheting mechanism 148 includes a first ratchet 150 disposed on the first proximal end portion 136 of the first arm 126 and a second ratchet 152 disposed on the second proximal end portion 146 of the second arm 128. As the first and second finger grips 134, 144 are moved toward each other, the first ratchet 150 engages with the second ratchet 152 to hold the first and second jaws 130, 140 together as they clamp onto the shank 110 of the hook 102.

To facilitate the clamping and securing of the hook 102, at least a part of the first and second jaws 130, 140 may extend at an obtuse angle 154 to a plane 156 substantially containing the rest of the first and second arms 126, 128. Alternatively, at least a part of the first and second jaws 130, 140 may extend at a substantially right angle 154 to the plane 156 substantially containing the rest of the first and second arms 126, 128.

The probe handle 118 of apparatus 100 is pivotally coupled to the forceps 116 at pivot joint 138. As such, for this particular example, the first arm 126, the second arm 128 and the probe handle 118 are pivotally coupled together at a single pivot joint 138. However, depending on design considerations, the probe handle 118 may be pivotally coupled to forceps 116 at a second pivot joint (not shown) as well.

The probe handle 118 includes a distal end portion 158 and a proximal end portion 160. The proximal end portion has a finger grip section 159 sized to engage a finger. Similar to the first and second arms 126, 128 of the forceps 116, the finger grip section 159 of the probe handle 118 is configured as a loop, but the finger grip section 159 may have other configurations as well.

For this particular example, the finger grip section 159 of the probe handle 118 and the first and second finger grip sections 134, 144 of the forceps 116 are configured to be gripped by a single hand of a user. For example, a user's thumb and index finger may grasp the first and second finger grip sections 134, 144 of the forceps 116, while the user's middle finger or ring finger may grasp the finger grip section 159 of the probe handle 118. As such, the removal of a hook 102, utilizing the apparatus 100, may be a one handed operation. Advantageously, a user may then be able to remove a hook (such as a fish hook) 102 that has been impaled in the users own body, even if he or she cannot use the other hand in the process.

The probe 120 is pivotally coupled to the distal end portion 158 of the probe handle 118. The tip portion 122 of the probe 120 is configured to fit within the space 124 between the barb 104 and the point section 106 of the hook 102. When the tip portion 122 is fit within the space 124 between the barb 104 and the point section 106 of the hook 102, the probe 120 and the barb 104 may form a sufficiently smooth, continuous and/or substantially planar surface 162, which may enable the hook 102 to be removed from the tissue 184 without the barb 104 preventing such removal.

The barb 104 includes a lower surface 123 and an upper surface 125 that intersect at a sharp angle to form the point 115 of the barb 104. The lower surface 123 of the barb 104 and the point section 106 of the hook 102 form the space 124 therebetween.

The tip portion 122 of the probe 120 is contoured to fit within, and substantially fill, the space 124 between the lower surface 123 of the barb 104 and the point section 106 of the hook 102. More specifically, the tip portion 122 includes a protrusion 200 (best seen in FIG. 1C). The protrusion has a sloped surface 201 that is configured to abut against the point 115 of the barb 104 such that the point 115 and the sloped surface 201 form a portion of the sufficiently smooth, continuous and/or substantially planar surface 162. The remainder of the sufficiently smooth, continuous and/or substantially planar surface 162 is formed by the upper surface 125 of the barb 104.

The sloped surface 201 of the protrusion 200 is sloped to fit within the space 124 between the barb 104 and the point section 106 of the hook 102. The protrusion 200 also includes an apex 202. When the protrusion is inserted into the space 124, the height of the apex 202 extends above the level of the top surface 125 of the barb 104. Therefore, the protrusion 200 forms a bump that functions to lift the tissue 184 (best seen in FIG. 6) off of the barb 104 and to substantially reduce contact between the tissue 184 and the barb 104 as the hook 102 is removed from a wound 188.

To facilitate the formation of the sufficiently smooth, continuous and/or substantially planar surface 162 between the barb 104 and the probe 120, a spring mechanism 164 is disposed on the distal end portion 158 of the probe handle 118. The spring mechanism 164 may operatively connect to the probe 120 and the distal end portion 158 of the probe handle 118. As such the spring mechanism 164 applies a force to the probe 120 to bias the tip portion 122 of the probe 120 against the barb 104 when the tip portion 122 of the probe 120 is inserted within the space 124 between the barb 104 and the point section 106 of the hook 102.

In this example, the probe 120 is configured to be removably coupled to the distal end portion 158 of the probe handle 118. As will be discussed in greater detail with reference to FIG. 3 herein, the distal end portion 158 of the probe handle 118 includes a receiver section 166 to enable coupling and uncoupling the probe 120 from the probe handle 118.

Figure 2A:
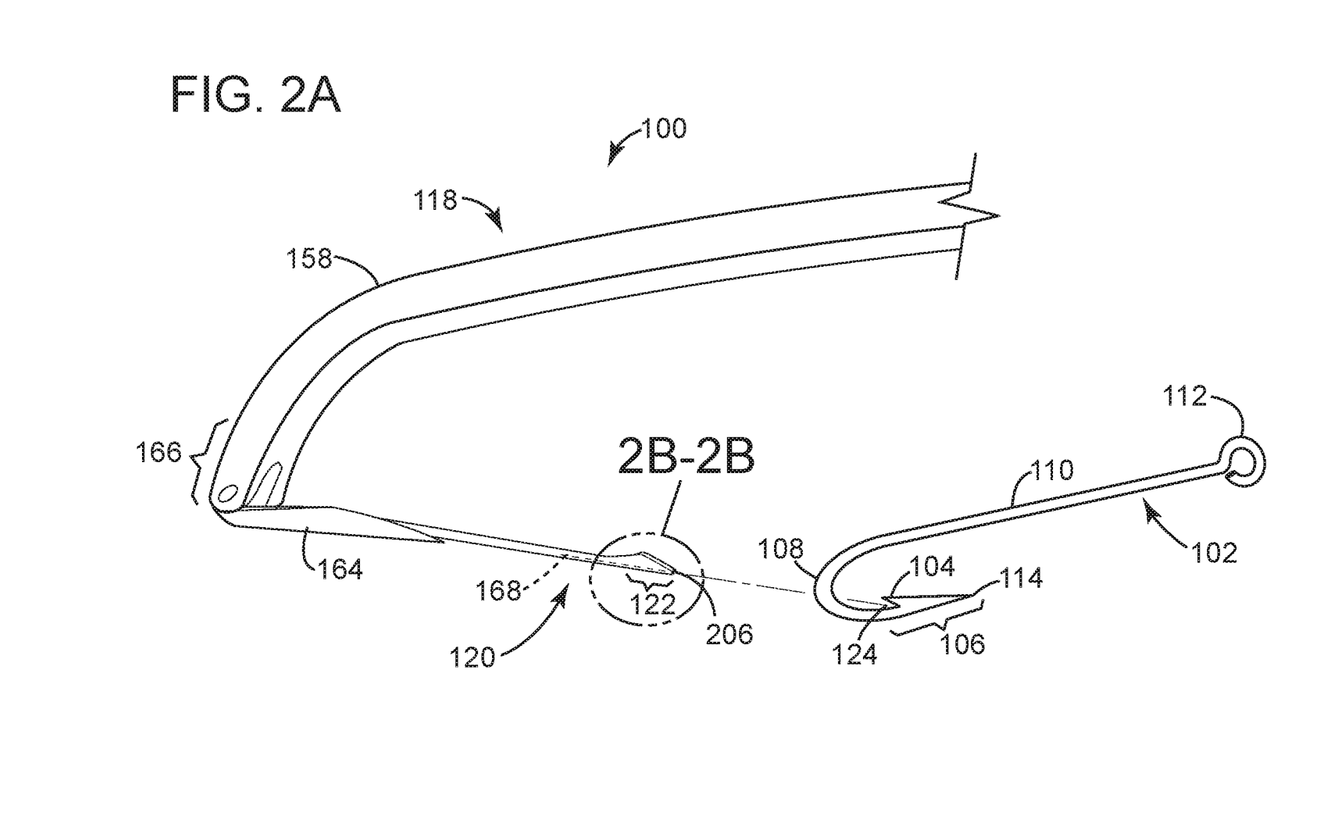
FIG. 2A depicts a perspective view of an example of a tip portion of a probe of the apparatus, wherein the probe is in the process of engaging a barb, and wherein the tip portion includes a notch disposed on the distal end of the tip portion according to aspects described herein.
Figures 2B, 2C:
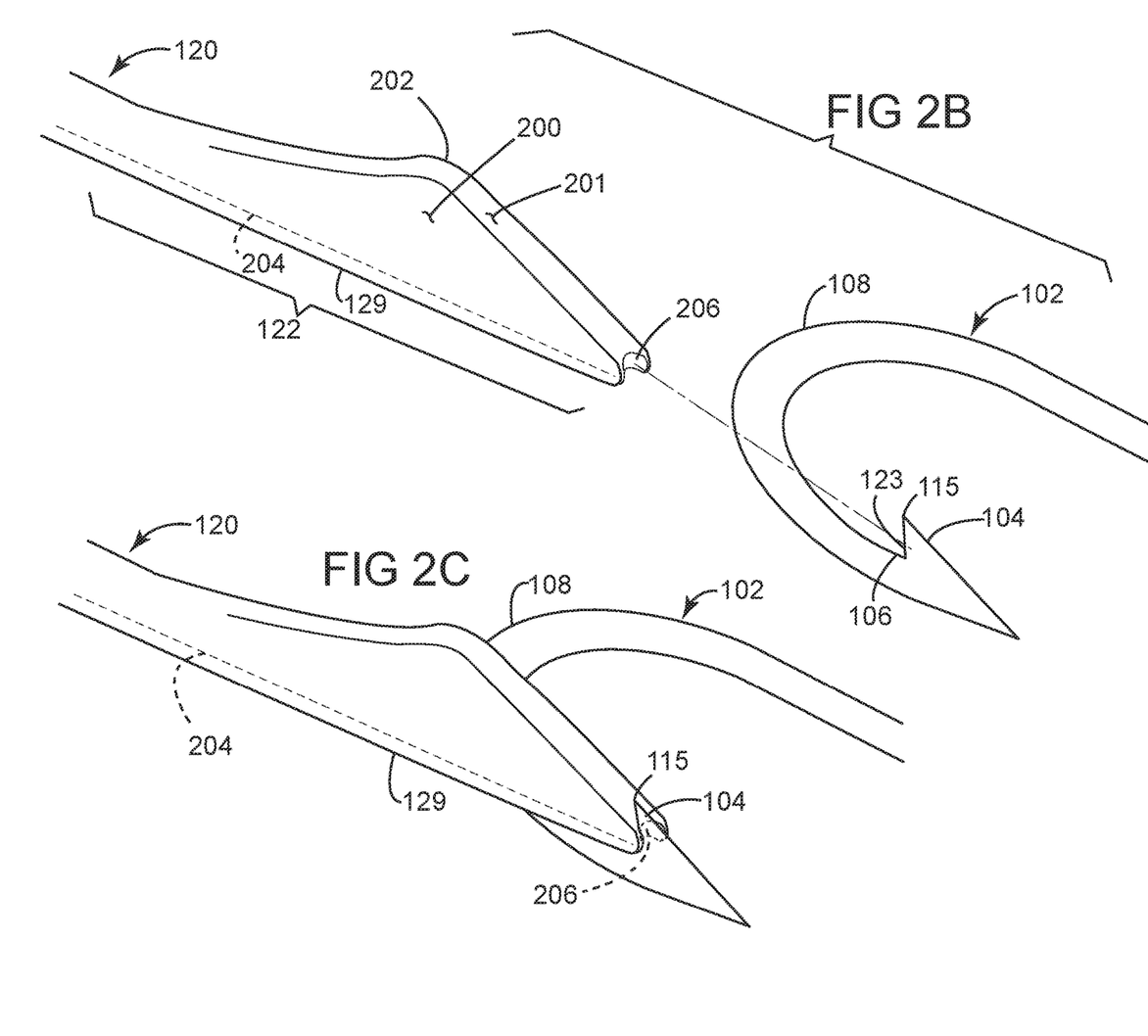
FIG. 2B depicts an expanded view of the circled area 2B-2B of FIG. 2A, wherein the tip portion of the probe is not engaged with the barb according to aspects described herein.
FIG. 2C depicts an expanded view of the circled area 2B-2B of FIG. 2A, wherein the tip portion of the probe is engaged with the barb according to aspects described herein.

Referring to FIGS. 2A, 2B and 2C, wherein FIG. 2A depicts a perspective view of an example of a tip portion 122 of a probe 120 engaging a barb 104, wherein the tip portion 122 includes a notch 206 disposed on the distal end of the protrusion 200 according to aspects described herein. Additionally, FIG. 2B depicts an expanded perspective view of the circled area 2B-2B of FIG. 2A, wherein the tip portion 122 of the probe 120 and the notch 206 are disengaged from the barb 104. Additionally, FIG. 2C depicts an expanded front view of the notch 206 of FIG. 2B, wherein the tip portion 122 of the probe 120 and the notch 206 are engaged with the barb 104.

The tip portion 122 also includes a notch 206, which is disposed at the distal end of the tip portion 122 of the probe 120. The notch 206 is sized to fit within the space 124 between the bard 104 and the point section 106 of the hook 102. The notch is also sized to straddle the barb 104 in order to help prevent the probe 120 from sliding sideways off of the hook 102. More specifically, the notch 206 straddles the barb 104 where the lower surface 123 of the barb 104 meets the point section 106 of the hook 102.

Figure 3A:
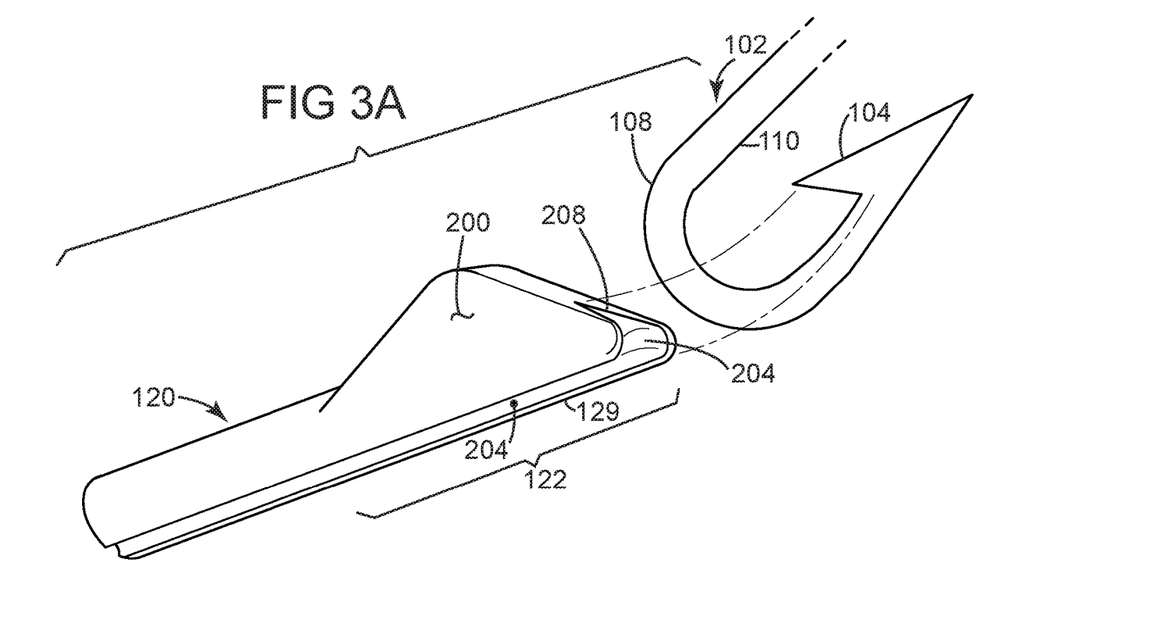
FIG. 3A depicts a perspective view of an example of a tip portion of a probe engaging a barb, wherein the tip portion includes a groove disposed on a sloped surface of a protrusion, wherein a slot is disposed on a lower surface of the tip portion, and wherein the tip portion is not engaged with the barb, according to aspects described herein.
Figure 3B:
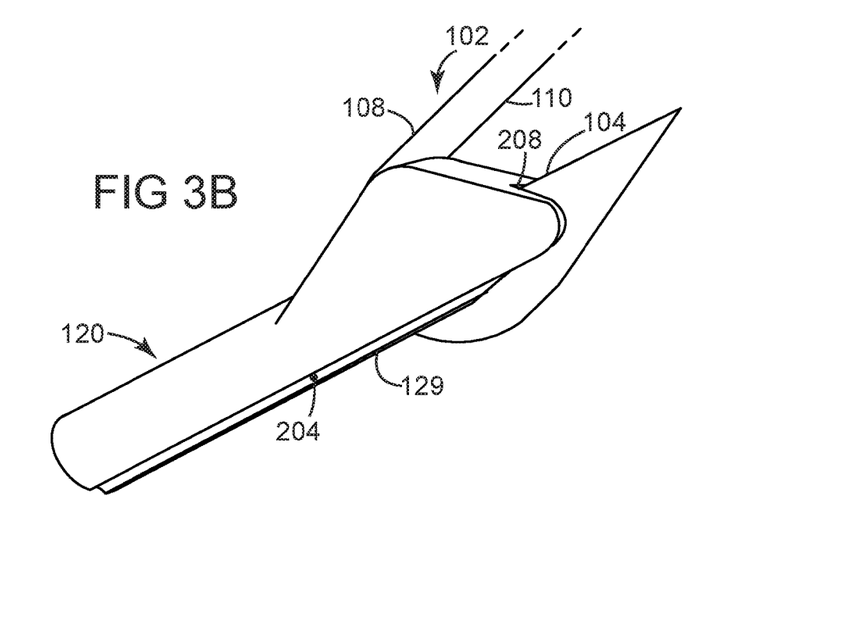
FIG. 3B depicts an expanded perspective view of the tip portion of the probe of FIG. 3A, wherein the tip portion is engaged with the barb according to aspects described herein.

Referring to FIGS. 3A and 3B, wherein expanded views of an example of the tip portion 122 of the probe 120 are depicted. More specifically, FIG. 3A depicts an expanded view an example of the tip portion 122 of the probe 120 having slot 204, wherein the tip portion 122 is disengaged from the barb 104. Also, more specifically, FIG. 3B depicts an expanded view of the tip portion 122 of FIG. 3A, wherein the portion 122 is engaged with the barb 104.

The tip portion 122 also includes a slot 204 disposed on a lower surface 129 of the tip portion. That is, the slot 204 is positioned on the surface 129, which is on the side of the tip portion 122 that is opposite to that of the protrusion 200. The slot 204 is sized to engage the bend section 108 of the shank 110. The slot 204 functions as a guide for the probe 102 to slide down the shank 110 to the barb 104. The slot 204 also functions to keep the probe 102 from sliding sideways off of the shank 110 of the hook 102.

The example of apparatus 100, as illustrated in FIGS. 3A and 3B, includes a tip portion 122 disposed at the end of the probe 120 which has a groove 208 disposed on the sloped surface 201 of protrusion 200. The groove 208 of protrusion 200 is configured to receive the barb 104 of the hook 102 therein. When the groove 208 engages the barb 104, the groove 208 cups the barb 104 to help prevent the tip portion 122 of the probe 120 from inadvertently sliding out sideways from the space 124 between the barb 104 and the point section 106 of the hook 102.

The groove 208 is illustrated in this example as a tapered groove 208. However, various alternative shaped grooves may also be used to help prevent the tip portion 122 from disengaging from the barb 104. For example, the groove may be concave shaped, V shaped, circular shaped, rectangular shaped or the like.

Figure 4:
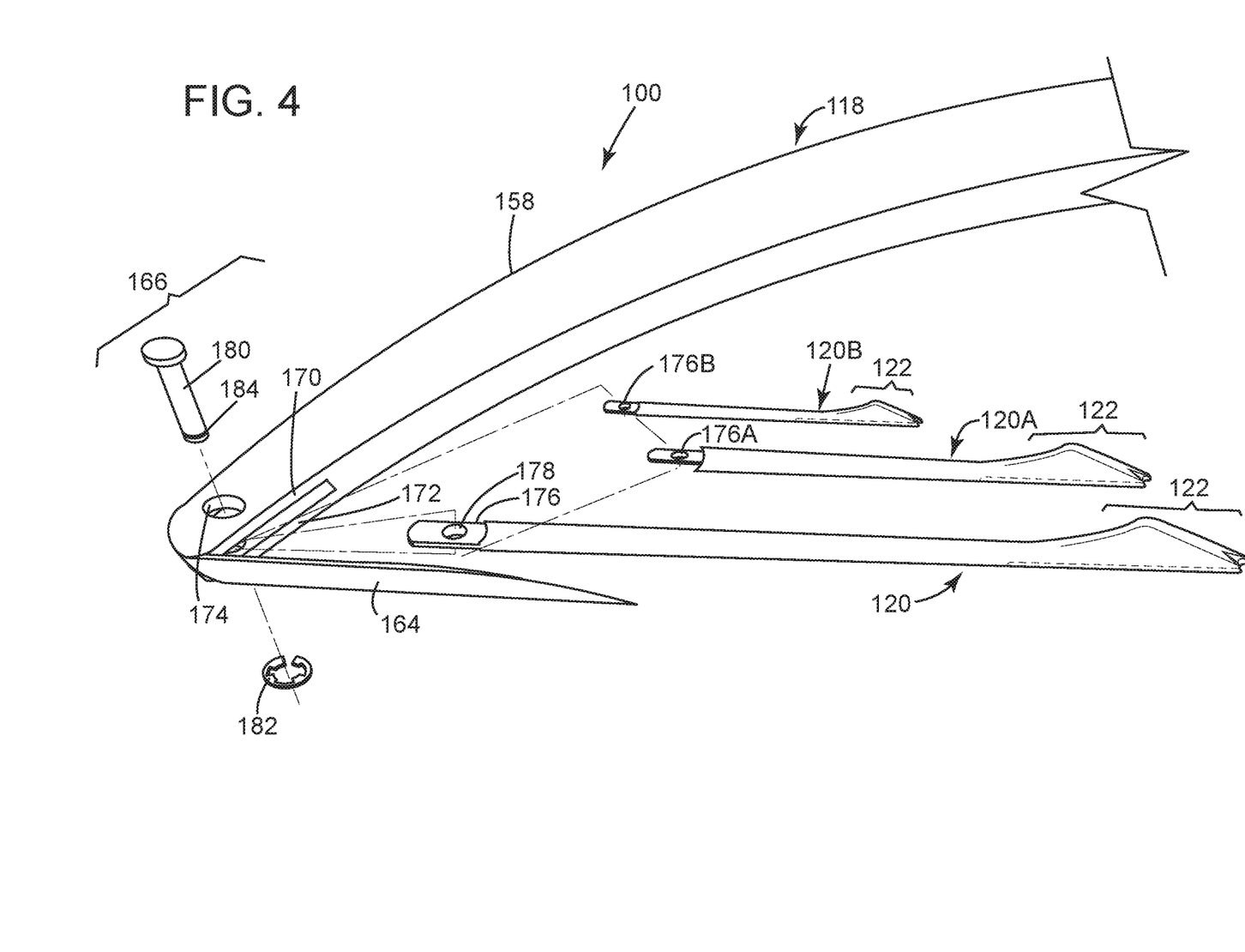
FIG. 4 depicts an exploded view of a probe pivotally coupled to a distal end portion of a probe handle according to aspects described herein.

Referring to FIG. 4, an exploded view of an example of the probe 120 pivotally coupled to the distal end portion 158 of the probe handle 118 is depicted. In this example the distal end portion 158 of the probe handle 118 includes the receiver section 166 for coupling and uncoupling the probe 120 from the probe handle 118.

The receiver section 166 is bifurcated into substantially parallel first and second branches 170 and 172. Each branch 170, 172 has a through hole 174 disposed therethrough, wherein the through holes 174 are substantially aligned with each other.

The probe 120 includes a mounting portion 176 sized to fit between the first and second branches 170, 172. The mounting portion 176 also has a through hole 178 disposed therethrough. When the mounting portion 176 of the probe 120 is placed between the first branch 170 and the second branch 172 of the probe handle 118, the through hole 178 of the mounting portion 176 is substantially aligned with the through holes 174 of the first and second branches 170, 172.

The mounting portion 176 in this example is illustrated as being disposed at an extreme end of the probe 120 that is opposite the extreme end of the probe having the tip portion 122 disposed thereon. However, the mounting portion 176 may also be disposed medially between the two extreme ends of the probe 120.

A mounting pin 180 is sized to slidably fit through the through holes 174, 178 of the first branch 170, the second branch 172 and the mounting portion 176 when the probe 120 is coupled to the receiver section 166. As such, the mounting pin 180 is configured to pivotally support the probe 120 within the receiver section 166 when the probe is coupled to the receiver section 166. Additionally, the mounting pin 180 is configured to be removed from the receiver section 166 in order to uncouple the probe 120 from the receiver section 166.

The mounting pin 180 is shown as a pin with a head on one end in FIG. 3. However, the mounting pin 180 may have a variety of other configurations. For example, the mounting pin 166 may be configured as a pivot bolt and nut assembly.

A retaining fastener 182 operatively engages with the mounting pin 180 when the mounting pin 180 is inserted through the through holes 174 of the first and second branches 170, 172 and the through hole 178 of the mounting portion 176 in order to couple the probe 120 to the probe handle 118. The retaining fastener 182 prevents the mounting pin 180 from inadvertently sliding out of the through holes 174, 178 when the apparatus 100 is in use.

In the example of FIG. 4, the retaining fastener 182 is configured as a retaining ring or snap ring that engages an annular groove 184 on a distal end of the mounting pin 180. However, the retaining fastener may have a variety of other configurations as well. For example, the retaining fastener 182 may be a cotter pin, a nut or the like.

In the example of FIG. 4, a single probe 120 is illustrated as being removably coupled to the receiver section 166 of the probe handle 118. However, the apparatus 100 can be configured to include a plurality of probes 120, 120A, 120B having a plurality of sizes and shapes, wherein each probe is configured to be removably coupled to the distal end portion 158 of the probe handle 118. More specifically, the probes 120, 120A, 120B will have mounting portions 176 that are sized to fit with receiver 166. The different probes 120, 120A, 120B may be designed to remove different sizes and styles of hooks 102 with different sizes of barbs 104 from tissues 184 when the probes 120, 120A, 120B are coupled to the distal end portion 158 of the probe handle 118.

Additionally, the different probes 120, 120A, 12B may be composed of different materials to accommodate different applications. For example, the probe material may be made of a durable stainless steel to accommodate frequent use in fishing applications. Alternatively, the probe may be made of a surgical material for removal of hooks from human tissue.

Though the receiver section 166, in this example is illustrated as being designed to accommodate a mounting pin 180, other forms of receiver sections may also be used. For example, the receiver section 166 may include a male or female threaded portion that is design to receive a probe 120 having mating threads disposed thereon.

FIGS. 5-8 illustrate various examples of a method of utilizing the apparatus 100 to remove a hook 102 with a barb 104 from tissue 184 according to aspects described herein.

Figures 5, 6:
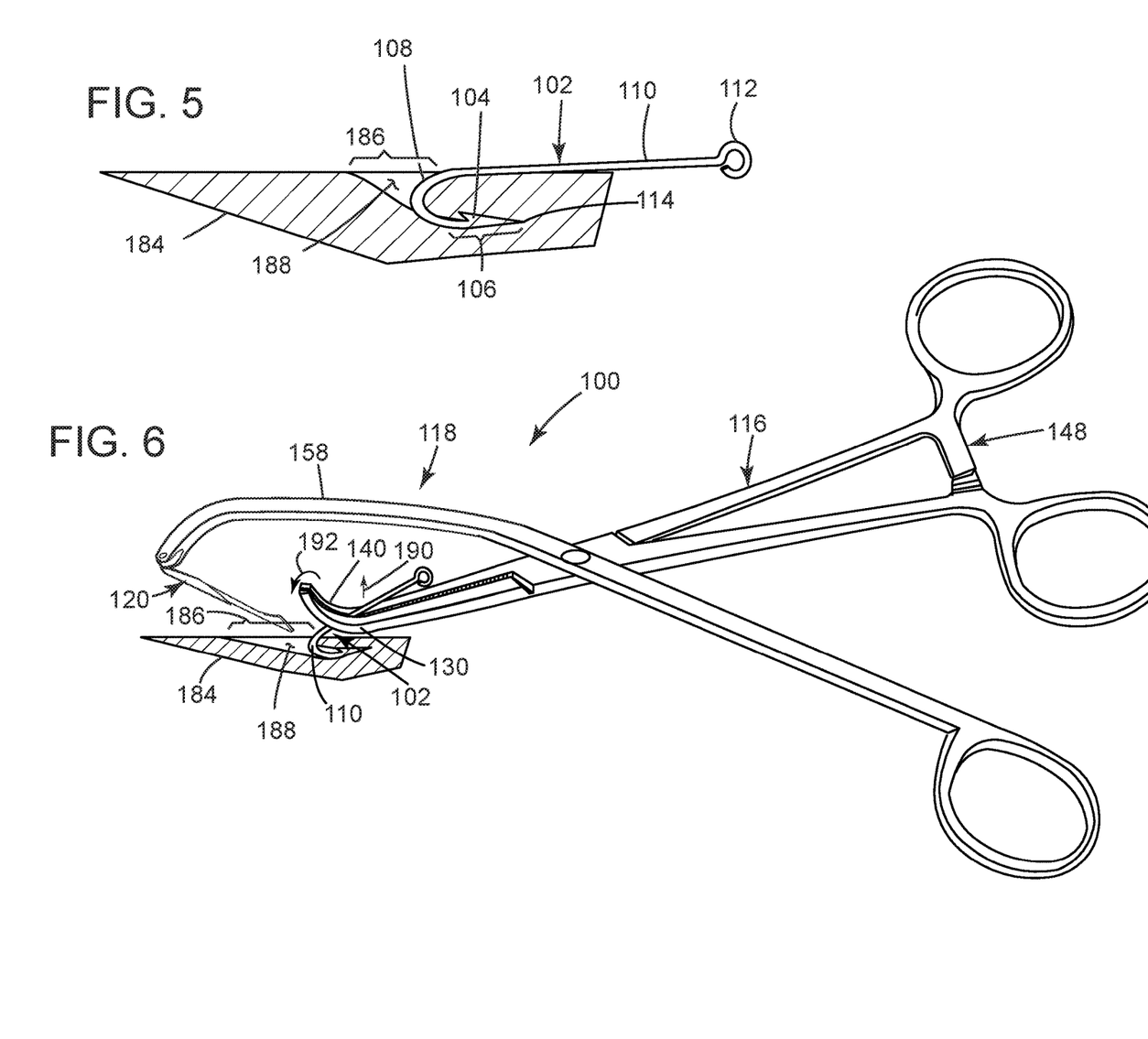
FIG. 5 depicts a perspective view of a hook with a barb embedded in tissue according to aspects described herein.
FIG. 6 depicts a perspective view of a clamping device of an apparatus for removing a hook grasping the hook of FIG. 5 according to aspects described herein.

Referring to FIG. 5, a perspective view of an example of a hook 102 with a barb 104 embedded in tissue 184 is depicted. The tissue 184 may be human tissue or animal tissue. The animal tissue may be any number of various animals, such as a fish, a mammal, a bird, a reptile, an amphibian or the like.

The hook 102, in this particular example, is a fish hook 102. The fish hook includes a point section 106 being integrally connected to a bend 108 of a shank 110, the bend being integrally connected to the straight portion of the shank 110 and the shank being integrally connected to an eye 112. The point section 106 includes a point 114 disposed at an extreme end of point section 106. A barb 104 is disposed on the point section 106 and extends in a direction opposed to the direction the point 114 extends in.

The point section 106 of the hook 102 is embedded into tissue 184. As such the hook has entered the tissue via its point 114 at an area of entry 186 on the tissue 184 to create a wound 188 in the tissue. Because the barb 104 extends in the opposite direction of the point 114, removing the point section 106 from the wound 188 without further tearing or damaging of the tissue 184 is problematic.

Referring to FIG. 6, a perspective view of a clamping device 116 of an apparatus 100 for removing a hook grasping the hook 102 of FIG. 5 is depicted. In order to remove the hook 102, the jaws 130, 140 of the clamping device (in this case, a forceps) 116 grasp the shank 110 of the hook 102 as the ratchet mechanism 148 locks the jaws together. At this stage of the removal procedure, the probe 120 has not yet been inserted into the wound 188 to engage the barb 104 of the hook 102.

The grasping of the hook 102 may be done in a one handed operation. That is, in this example, wherein the clamping device is a forceps 116, a user may insert his or her thumb and index finger into the finger grip sections 134, 144 in order to manipulate the forceps 116 and grasp the hook 102. Moreover, other forms of clamping devices 116 (for example, needle nose pliers) may be configured to be operated in a similar one handed fashion.

After the forceps 116 grasp the shank 110 of the hook 102, the hook 102 is then maneuvered to facilitate the engagement of the probe 120 with the barb 104. Essentially, the forceps 116 maneuver the hook 102 to bring the barb 104 closer to the outside surface of the tissue 184 and to correctly position the hook 102 to receive the probe 120 as it is advanced into the barb 104.

The maneuvering of the hook 102 can be accomplished in a variety of ways. For example, the hook 102 may be lifted upward (as indicated by arrow 190) relative to the tissue 184 to bring the barb 104 closer to the area of entry 186. Alternatively for example, the hook 102 may be twisted (as indicated by arrow 192) to enlarge the area of entry 186. By either bringing the hook 102 closer to the area of entry 186, or enlarging the area of entry 186, it becomes easier for the probe 120 to be inserted into the area of entry 186 of the wound 188 to engage the barb 104.

Figure 7:
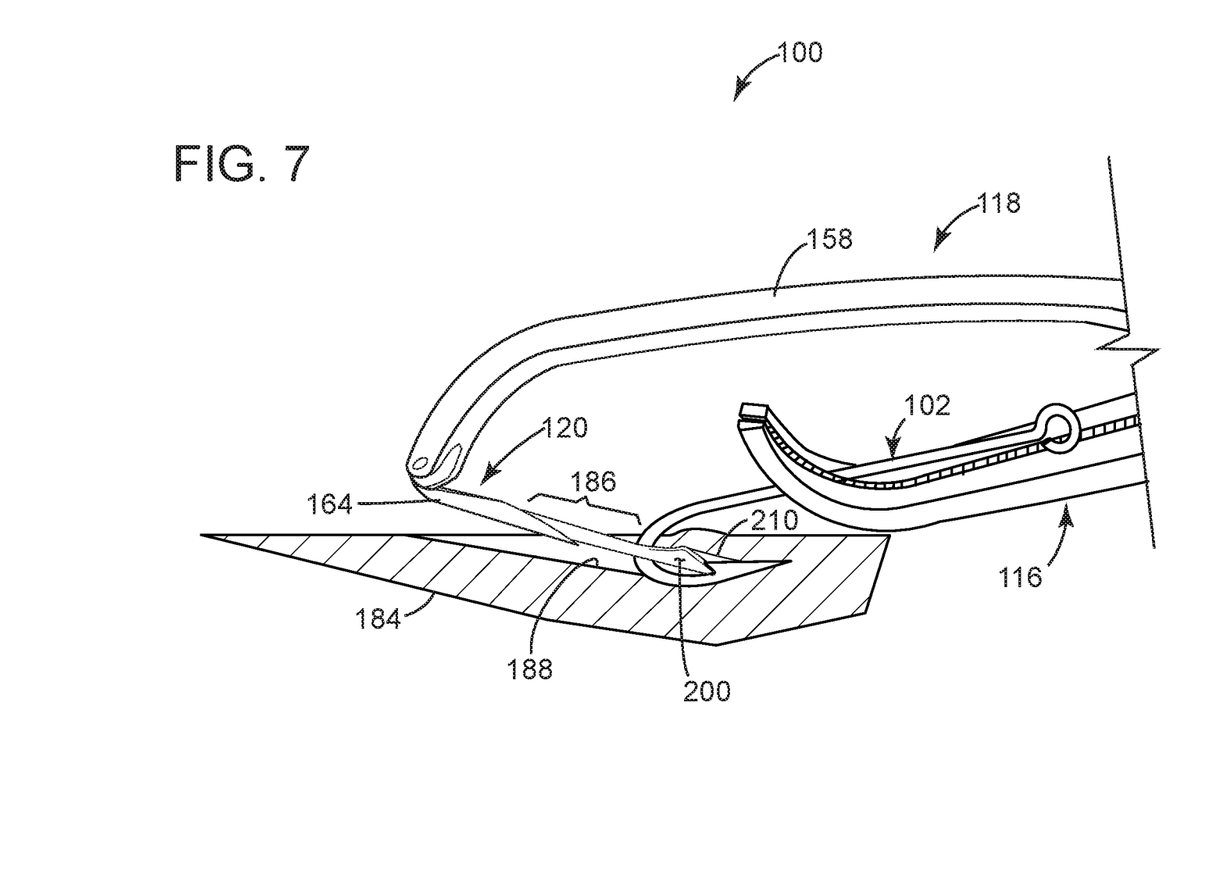
FIG. 7 depicts an expanded perspective view of a probe of the apparatus of FIG. 6 engaging a barb of the hook of FIG. 5 according to aspects described herein.

Referring to FIG. 7, an expanded perspective view of the probe 120 of the apparatus 100 of FIG. 6 engaging the barb 104 of the hook 102 of FIG. 5 is depicted. At this stage of the removal procedure, the tip portion 122 of the probe 120 may be inserted into the area of entry 186 of the wound 188 and into engagement with the barb 104.

The inserting of the tip portion 122 of the probe 120 may also be done in a one handed operation. That is, in this example, a user may insert his or her middle or ring finger into the finger grip section 159 of the probe handle 118 in order to manipulate the probe handle 118 to insert the tip portion 122 into the area of entry 186 of the wound 188. This may be done while the user uses the thumb and index finger to manipulate the clamping device 116 and grasp the hook 102.

More specifically, the tip portion 122 of the probe 120 is fit within the space 124 between the barb 104 and the point section 106 of the hook 102. As such, the probe 120 and the barb 104 may form a sufficiently smooth, continuous and/or substantially planar surface 162. Additionally, the protrusion 200 lifts the tissue 184 away from the barb 104, which may create a small channel 210 between the barb 104 and the tissue 184. Additionally, the spring mechanism 164 applies a force to the probe 120 to bias the tip portion 122 of the probe 120 against the barb 104 in order to help maintain the sufficiently smooth, continuous and/or substantially planar surface 162 between the barb 104 and the probe 120.

The fitting of the probe 120 into the barb, may also be done in a one handed operation. That is, a user's thumb and index fingers may be used to manipulate the forceps (or other clamping device) 116 in order to grasp the hook 102. Simultaneously, the middle or ring finger may manipulate the probe handle 118 in order to fit the probe 120 within the space 124 between the barb 104 and the point section 106 of the hook 102.

Figure 8:
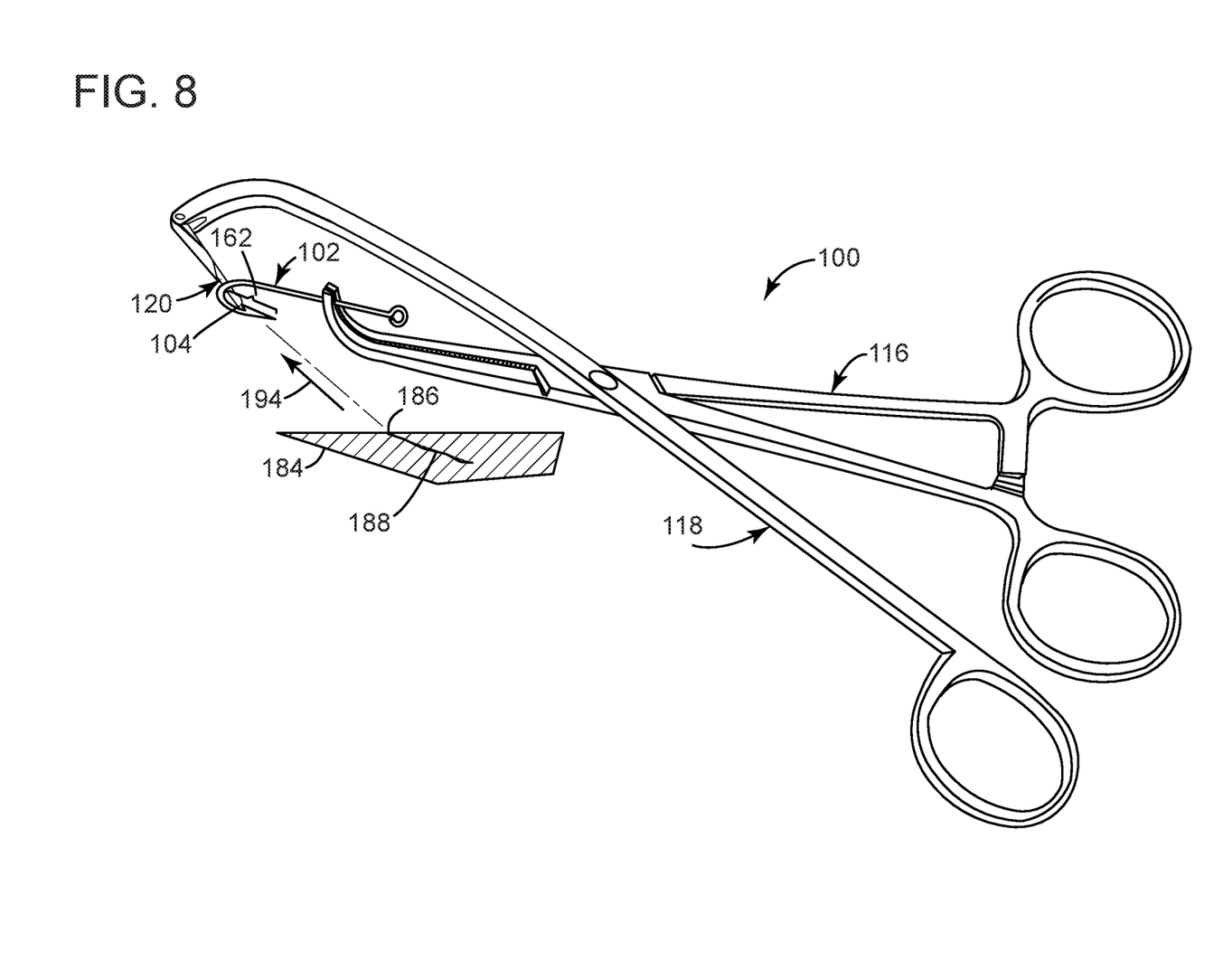
FIG. 8 depicts a perspective view of the apparatus of FIG. 7 removing the hook of FIG. 5 from the tissue according to aspects described herein.

Referring to FIG. 8, a perspective view of the apparatus 100 of FIG. 7 removing the hook 102 of FIG. 5 from the tissue 184 is depicted. Because of the sufficiently smooth, continuous and/or substantially planar surface 162 formed between the barb and the probe 120 and/or because of the protrusion 200 lifting the tissue 184 away from the barb 104, the hook 102 can now be removed from the wound 188 (as indicated by arrow 194). More specifically, the hook 102 can now be removed from the wound 188 with a significantly reduced risk of causing further damage to the tissue 184 compared to further damage to the tissue 184 caused by the hook 102 being removed without the probe 120.

The removing of the hook 102 from the tissue 184 may also be done in a one handed operation. That is, the user's thumb and index fingers may be used to manipulate the clamping device 116 in order to keep the hook 102 grasped firmly between the jaws 130, 140 of the clamping device. Then the user's middle or ring finger may be used to manipulate the probe handle 118 in order to keep the probe 120 firmly fitted within the space 124 between the barb 104 and the point section 106 of the hook 102. Then the user may remove the hook 102 with the same single hand that is used to manipulate the clamping device 116 and probe handle 118.

Although the disclosure has been described by reference to specific examples, it should be understood that numerous changes may be made within the spirit and scope of the inventive concepts described. Accordingly, it is intended that the disclosure not be limited to the described examples, but that it have the full scope defined by the language of the following claims.

What is claimed is:

1. An apparatus for removing a hook, the hook having a shank that is connected to a point section, said point section defining a point disposed at the point section's distal end, the hook also having a barb that extends in a direction away from the point of said point section, said barb defining a point at the distal end of said barb, the apparatus comprising:
   a clamping device configured to secure the hook; and
   a probe held by the clamping device, the probe having a tip portion configured to fit between the barb and the point section of the hook, said tip portion fitting in the space between the barb and the point section of the hook, said tip portion defining a sloped surface with an upper end such that, at times when the tip portion is inserted in the space between the barb and the point section of the hook, a portion of the sloped surface extends above the point of the barb;
   a notch that is disposed on a distal end of said tip portion, said notch being sized to straddle the barb at times when the tip portion is inserted between the barb and the point section of the hook; and
   a slot located on an opposite side of the tip portion from the sloped surface, the slot extending from the notch longitudinally along the tip portion for a length at least equal to the dimension between the notch and the upper end of said sloped surface, the slot being sized to engage the shank of the hook such that the slot guides the probe to move along the shank.

2. The apparatus of claim 1, wherein the probe is pivotably coupled to the clamping device such that the probe pivots relative to the clamping device.

3. The apparatus of claim 1, wherein, when the tip portion is fit between the barb and the point section of the hook, said probe and said barb form a continuous surface.

4. The apparatus of claim 1, further comprising a probe handle pivotably coupled to the clamping device, the probe handle including:
   a distal end portion pivotably coupled to the probe; and
   a proximal end portion having a finger grip section.

5. An apparatus for removing a hook, said hook defining a shank that is connected to a point section, the point section of said hook extending to a point that is disposed at the distal end of the point section, said hook also defining a barb that extends in a direction away from the point of said point section, said barb defining a point at the distal end of said barb, the apparatus comprising:
   a forceps configured to secure the hook, the forceps including:
      a first arm having a first jaw disposed on a first distal end portion and a first finger grip section disposed on a first proximal end portion, and
      a second arm pivotally connected to the first arm, the second arm having a second jaw disposed on a second distal end portion and a second finger grip section disposed on a second proximal end portion;
   a probe handle that is pivotally coupled to the forceps, the probe handle including a distal end portion and a proximal end portion, the proximal end portion of said probe handle having a finger grip section; and
   a probe that is pivotally coupled to the distal end portion of the probe handle, the probe having a tip portion that is configured to fit between the barb and the point section of the hook, said tip portion including;
      a protrusion disposed on the tip portion, the protrusion including a sloped surface that fits between the barb and the point section of the hook, said protrusion also having an apex such that, at times when the protrusion is inserted between the barb and the point section of the hook, the apex is above the point of the barb;
      a notch disposed on a distal end of the tip portion, the notch being sized to straddle the barb at times when the tip portion is inserted between the barb and the point section of the hook; and
      a slot in a lower surface of the tip portion that is opposite on the tip portion from the protrusion, the slot extending from the notch longitudinally along the tip portion for a length at least equal to the dimension between the notch and the apex of the protrusion, the slot being sized to engage the shank of the hook such that the slot guides the probe along the shank to the barb.

6. The apparatus of claim 5, further comprising a spring mechanism connected to the probe and to the distal end portion of the probe handle, the spring mechanism biasing the tip portion of the probe against the barb when the tip portion of the probe is inserted between the barb and the point section of the hook.

7. The apparatus of claim 5, wherein the probe is removably coupled to the distal end portion of the probe handle.

8. The apparatus of claim 5, further comprising a plurality of probes of different sizes, each of the plurality of probes configured to be removably coupled to the distal end portion of the probe handle.

9. An apparatus for removing a hook, the hook having a shank with a bend section that is connected to a point section, said point section defining a point that is disposed at the distal end of the point section, the hook also having a barb that extends in a direction away from said point, said barb defining a point at the distal end of said barb, the apparatus comprising:
   a clamping device configured to secure the hook; and
   a probe held by the clamping device, the probe having a tip portion configured to fit between the barb and the point section of the hook, said tip portion defining a sloped surface that fits between the barb and the point section of the hook, said tip portion also defining a sloped surface that has an upper end such that when the tip section is inserted between the barb and the point section of the hook, a portion of the sloped surface extends above the point of the barb;
      a notch disposed on a distal end of said tip portion, said notch being sized to straddle the barb at times when the tip portion is inserted between the barb and the point section of the hook; and,
      a groove disposed on the sloped surface of the tip portion, said groove extending along said tip portion from the notch through said sloped surface, said groove configured to receive the barb of the hook when the probe is inserted between the barb and the point section of the hook.

10. An apparatus for removing a hook, said hook having a shank connected to a point section, said point section having a distal end that defines a point, the hook also defining a barb that extends away from said point section, said barb having a distal end that defines a point, the apparatus comprising:
   a forceps configured to secure the hook, the forceps including:
      a first arm having a first jaw disposed on a first distal end portion and a first finger grip section disposed on a first proximal end portion, and
      a second arm pivotally connected to the first arm, the second arm having a second jaw disposed on a second distal end portion and a second finger grip section disposed on a second proximal end portion;
   a probe handle pivotally coupled to the forceps, the probe handle including a distal end portion and a proximal end portion that has a finger grip section; and
   a probe coupled to the distal end portion of the probe handle, the probe having a tip portion configured to fit between the barb and the point section of the hook, said tip portion including;
      a protrusion that includes a sloped surface that fits between the barb and the point section of the hook, said protrusion having an apex such that when the tip portion is inserted between the barb and the point section of the hook, a portion of the apex is above the point of the barb;
      a notch disposed on a distal end of the tip portion, the notch being sized to straddle the barb at times when the tip portion is inserted between the barb and the point section of the hook; and
      a groove disposed on the sloped surface of the protrusion and extending from the notch, said groove being configured to receive the barb of the hook when the tip portion is inserted between the barb and the point section of the hook.

11. An apparatus for removing a hook, said hook having a shank that is connected to a point section, said point section defining a point disposed at the distal end of the point section, the hook also having a barb extending in a direction away from of said point section, said barb defining a point at the distal end of the barb, the apparatus comprising:
   a clamping device configured to secure the hook; and a probe coupled to the clamping device, the probe including a tip portion that is configured to fit between the barb and the point section of the hook, said tip portion comprising:
- a notch in a distal end of the tip portion of the probe, the notch straddling the barb at times when the tip portion is inserted between the barb and the point section of the hook;
- a protrusion that defines a sloped surface and an apex, the sloped surface extending between the notch and the apex; and
- a slot in a surface of the tip portion that is on an opposite side of the tip portion from the protrusion, the slot extending from the notch longitudinally along the lower surface for a length equal to or greater than the dimension between the notch and the apex of the protrusion.

12. An apparatus for removing a hook that has a shank that is connected to a point section, the point section extending to a point that is disposed at the distal end of the point section, the hook also having a barb that extends in a direction away from the point section, said barb defining a point disposed at the distal end of the barb, the apparatus comprising:
- a clamping device configured to secure the hook; and
- a probe coupled to the clamping device, the probe comprising a tip portion configured to fit between the barb and the point section of the hook, the tip portion comprising:
    - a notch disposed on a distal end of the tip portion, the notch being sized to straddle the barb when the tip portion is inserted between the barb and the point section of the hook;
    - a protrusion comprising a sloped surface and an apex, the sloped surface extending upwards from the notch to the apex; and
    - a groove disposed on the sloped surface of the protrusion and extending from the notch, the groove configured to receive the barb of the hook when the probe is inserted into the space between the barb and the point section of the hook.

* * * * *